(12) United States Patent
Potuluri et al.

(10) Patent No.: US 7,720,694 B2
(45) Date of Patent: May 18, 2010

(54) PHARMACEUTICAL VERIFICATION NETWORK

(75) Inventors: Prasant Potuluri, Raleigh, NC (US);
David J. Brady, Durham, NC (US);
Michael Fuller, Chapel Hill, NC (US)

(73) Assignee: Optopo Inc., Morrisville, NC (US)

( * ) Notice: Subject to any disclaimer, the term of this patent is extended or adjusted under 35 U.S.C. 154(b) by 600 days.

(21) Appl. No.: 11/609,443

(22) Filed: Dec. 12, 2006

(65) Prior Publication Data

US 2008/0059240 A1 Mar. 6, 2008

Related U.S. Application Data

(63) Continuation-in-part of application No. 11/454,923, filed on Jun. 19, 2006, now Pat. No. 7,218,395, which is a continuation-in-part of application No. 11/334,546, filed on Jan. 19, 2006, now Pat. No. 7,301,625, and a continuation-in-part of application No. 10/417,066, filed on Apr. 16, 2003, now Pat. No. 7,092,101.

(60) Provisional application No. 60/644,522, filed on Jan. 19, 2005, provisional application No. 60/705,173, filed on Aug. 4, 2005, provisional application No. 60/725,311, filed on Oct. 12, 2005, provisional application No. 60/811,101, filed on Jun. 6, 2006.

(51) Int. Cl.
*G06Q 10/00* (2006.01)

(52) U.S. Cl. .......................................................... 705/2

(58) Field of Classification Search ...................... 705/2
See application file for complete search history.

(56) References Cited

U.S. PATENT DOCUMENTS

| 6,202,923 B1 * | 3/2001 | Boyer et al. ................. 235/375 |
| 6,771,369 B2 * | 8/2004 | Rzasa et al. ................. 356/326 |
| 7,006,214 B2 | 2/2006 | Rzasa et al. |
| 2005/0077476 A1 | 4/2005 | Poteet et al. |
| 2006/0015536 A1 | 1/2006 | Buchanan et al. |

\* cited by examiner

*Primary Examiner*—Gerald J. O'Connor
*Assistant Examiner*—Hiep Nguyen
(74) *Attorney, Agent, or Firm*—John R. Kasha; Kasha Law LLC

(57) ABSTRACT

Embodiments of the present invention relate to systems and methods for communicating pharmaceutical verification information between a server and a node using a network. A node includes a pharmaceutical identification and verification system. The verification information includes a known spectral signature of a known pharmaceutical and a corresponding known pharmaceutical name and dosage strength of the known pharmaceutical. The server stores the verification information in a server database. The node receives the verification information from the server, stores the verification information in the client database, reads a pharmaceutical name and dosage strength from a container enclosing a pharmaceutical, obtains a detected spectral signature for the pharmaceutical, and compares the detected spectral signature to the at least one known spectral signature. The pharmaceutical identification and verification system includes a static multimodal multiplex spectrometer. The verification information can also include a spectral signature of a known container.

34 Claims, 11 Drawing Sheets ized patent application Ser. No. 11/454,923, filed Jun. 19,
PHARMACEUTICAL VERIFICATION NETWORK

CROSS-REFERENCE TO RELATED APPLICATION

This application is a continuation-in-part application of U.S. patent application Ser. No. 11/454,923, filed Jun. 19, 2006 now U.S. Pat. No. 7,218,395 (the "'923 application"). The '923 application is a continuation-in-part application of U.S. patent application Ser. No. 10/417,066 now U.S. Pat. No. 7,092,101 (the "'101 patent"), filed Apr. 16, 2003, and a continuation-in-part application of U.S. patent application Ser. No. 11/334,546 (the "'546 application), filed Jan. 19, 2006 now U.S. Pat. No. 7,301,625. The '546 application claims the benefit of U.S. Provisional Patent Application No. 60/644,522, filed Jan. 19, 2005, and U.S. Provisional Patent Application No. 60/705,173, filed Aug. 4, 2005. The '923 application claims the benefit of U.S. Provisional Patent Application No. 60/725,311, filed Oct. 12, 2005, U.S. Provisional Patent Application No. 60/811,101, filed Jun. 6, 2006. All of the above mentioned applications are incorporated by reference herein in their entireties.

BACKGROUND OF THE INVENTION

1. Field of the Invention

Embodiments of the present invention relate to systems and methods for prescription or pharmaceutical compound verification. More particularly, embodiments of the present invention relate to systems and methods for communicating with pharmaceutical identification and verification systems across a network.

2. Background Information

Most states in the U.S. require that a registered pharmacist confirm whether a pharmaceutical delivered to a customer is indeed the pharmaceutical prescribed by the physician. A part of this confirmation is accomplished by the pharmacist visually inspecting the dispensed pharmaceutical to verify its correctness. In fact, pharmacists can spend as much as 50% of their time verifying prescriptions.

Despite the verification process, errors are not uncommon, especially during peak operating hours. For example, according to the National Association of Boards of Pharmacy, as many as 5% of the 3 billion prescriptions filled each year are incorrect. These erroneous prescriptions are responsible for as many as 7,000 deaths annually in the United States. Further, due to a steadily decreasing number of pharmacists, and an expected increase in the annual demand for prescriptions to nearly 5 billion, the number of instances in which a customer receives the wrong medication is anticipated to increase.

Not surprisingly, increasing prescription errors have resulted in a growing collection of consumer complaints about potentially serious errors such as wrong counts, wrong drugs, and/or wrong dosages. Thus, there is a strong need for a system to replace the present manual verification technique and to allow the verification and validation steps to be performed automatically and more reliably. A by-product of such an automatic verification system is freeing up pharmacists' time so they can provide better service to their customers.

Several conventional automated prescription verification techniques have been developed to minimize errors associated with manual prescription verification. For example, conventional automatic visual verification techniques rely on the pharmacists comparing an electronic image of the prescribed medication, i.e., a picture of the prescribed medication retrieved from a data library, to the actual medication that is to be dispensed to a customer. These visual identification methods rely on the incorrect assumption that all pharmaceuticals are visually very distinct. In fact the visual difference between pharmaceuticals may be so subtle that errors are likely to occur even when comparing the contents of the prescription vial to a picture on a computer screen.

Spectroscopic analysis is a more reliable method of validating dispensed pharmaceuticals than using subjective visual techniques. Spectroscopic techniques rely on the unique spectral signature exhibited by each pharmaceutical, such as a pill, tablet, capsule, gelcap, gel, and liquid. Representative, non-limiting spectroscopic techniques for pharmaceutical verification include Near-Infrared (NIR) spectroscopy, ultraviolet (UV) and visible spectroscopy, Raman spectroscopy, and Fourier Transform Infrared (FT-IR) spectroscopy.

In order for a spectroscopic system to be able to verify a large number of prescriptions, the database of the spectroscopic system must contain a large amount of information about a large number of known pharmaceuticals. In view of the foregoing, it can be appreciated that a substantial need exists for systems and methods that can communicate with pharmaceutical identification and verification systems across a network.

BRIEF SUMMARY OF THE INVENTION

One embodiment of the present invention is a system for communicating pharmaceutical verification information where the spectral signature database information and verification transaction information is stored at each node and a node includes a static multimode multiplex spectrometer. The system includes a network a server database, a server, a client database, and a pharmaceutical identification and verification system. The pharmaceutical identification and verification system is, for example, a node. The server is connected to the network and the server database. The server stores at least one known spectral signature of a known pharmaceutical and a corresponding known pharmaceutical name and dosage strength of the known pharmaceutical in the server database. The pharmaceutical identification and verification system is connected to the network and the client database. The pharmaceutical identification and verification system includes a static multimode multiplex spectrometer. The pharmaceutical identification and verification system receives the at least one known spectral signature and the corresponding known pharmaceutical name and dosage strength from the server, stores the at least one known spectral signature and the corresponding known pharmaceutical name and dosage strength in the client database, reads a pharmaceutical name and dosage strength from a container enclosing a pharmaceutical, obtains a detected spectral signature for the pharmaceutical, and compares the detected spectral signature to the at least one known spectral signature.

Another embodiment of the present invention is a method for communicating pharmaceutical verification information between a server and a node where the spectral signature database information and verification transaction information is stored at each node and a node includes a static multimode multiplex spectrometer. A node is a pharmaceutical identification and verification system, for example. The server stores at least one known spectral signature of a known pharmaceutical and a corresponding known pharmaceutical name and dosage strength of the known pharmaceutical in a server database connected to the server. The server is connected to a network. The node receives the at least one known spectral signature and the corresponding known pharmaceutical name and dosage strength from the server. The node is connected to the network and a client database. The node stores at least one known spectral signature and the corresponding known pharmaceutical name and dosage strength in the client database. The node reads a pharmaceutical name and dosage strength from a container enclosing a pharmaceutical. The node obtains a detected spectral signature for the pharmaceutical. The node compares the detected spectral signature to at least one known spectral signature.

Another embodiment of the present invention is a system for communicating pharmaceutical verification information where the spectral signature database information and verification transaction information is stored at each node and the spectral signature database information includes information about a pharmaceutical container. The system includes a network, a server database, a server, a client database, and a pharmaceutical identification and verification system. The pharmaceutical identification and verification system is, for example, a node. The server is connected to the network and the server database. The server stores at least one known spectral signature that includes a spectral signature of a known pharmaceutical and a spectral signature of a known container. The server also stores a corresponding known pharmaceutical name and dosage strength of the known pharmaceutical in the server database. The pharmaceutical identification and verification system is connected to the network and the client database. The pharmaceutical identification and verification system receives the at least one known spectral signature and the corresponding known pharmaceutical name and dosage strength from the server, stores the at least one known spectral signature and the corresponding known pharmaceutical name and dosage strength in the client database, reads a pharmaceutical name and dosage strength from a container enclosing a pharmaceutical, obtains a detected spectral signature that includes a spectral signature of the pharmaceutical and a spectral signature of the container, and compares the detected spectral signature to the at least one known spectral signature.

Another embodiment of the present invention is a method for communicating pharmaceutical verification information between a server and a node where the spectral signature database information and verification transaction information is stores at each node and the spectral signature database information includes information about a pharmaceutical container. A node is a pharmaceutical identification and verification system, for example. The server stores at least one known spectral signature that includes a spectral signature of a known pharmaceutical and a spectral signature of a known container and a corresponding known pharmaceutical name and dosage strength of the known pharmaceutical in a server database connected to the server. The server is connected to a network. The node receives the at least one known spectral signature and the corresponding known pharmaceutical name and dosage strength from the server. The node is connected to the network and a client database. The node stores at least one known spectral signature and the corresponding known pharmaceutical name and dosage strength in the client database. The node reads a pharmaceutical name and dosage strength from a container enclosing a pharmaceutical. The node obtains a detected spectral signature that includes a spectral signature of the pharmaceutical and a spectral signature of the container. The node compares the detected spectral signature to at least one known spectral signature.

Another embodiment of the present invention is a system for communicating pharmaceutical verification information where the spectral signature database information and verification transaction information is centrally stored and analyzed and a node includes a static multimode multiplex spectrometer. The system includes a network, a server database, a server, and a pharmaceutical identification and verification system. The pharmaceutical identification and verification system is, for example, a node. The pharmaceutical identification and verification system is connected to the network. The pharmaceutical identification and verification system includes a static multimode multiplex spectrometer. The pharmaceutical identification and verification system reads a pharmaceutical name and dosage strength from a container enclosing a pharmaceutical and obtains a detected spectral signature for the pharmaceutical. The server is connected to the network and the server database. The server receives the pharmaceutical name and dosage strength and the detected spectral signature from the pharmaceutical identification and verification system, compares the detected spectral signature to one or more known spectral signatures of known pharmaceuticals in the server database to determine an identity of the pharmaceutical, compares a known pharmaceutical name and dosage strength corresponding to a known spectral signature of a known pharmaceutical that matches the detected spectral signature to the pharmaceutical name and dosage strength to verify the pharmaceutical, and sends a result of the verification to the pharmaceutical identification and verification system.

Another embodiment of the present invention is a method for communicating pharmaceutical verification information between a server and a node where the spectral signature database information and verification transaction information is centrally stored and analyzed by the server and a node includes a static multimode multiplex spectrometer. A node is a pharmaceutical identification and verification system, for example. The node reads a pharmaceutical name and dosage strength from a container enclosing a pharmaceutical. The node is connected to a network and includes a static multimode multiplex spectrometer. The node obtains a detected spectral signature for the pharmaceutical. The server receives the pharmaceutical name and dosage strength and the detected spectral signature from the pharmaceutical identification and verification system. The server is connected to the network and a server database. The server compares the detected spectral signature to one or more known spectral signatures of known pharmaceuticals in the server database to determine an identity of the pharmaceutical. The server compares a known pharmaceutical name and dosage strength corresponding to a known spectral signature of a known pharmaceutical that matches the detected spectral signature to the pharmaceutical name and dosage strength to verify the pharmaceutical. The server sends a result of the verification to the node.

Another embodiment of the present invention is a system for communicating pharmaceutical verification information where the spectral signature database information and verification transaction information is centrally stored and analyzed and the spectral signature database information includes information about a pharmaceutical container. The system includes a network, a server database, a server, and a pharmaceutical identification and verification system. The pharmaceutical identification and verification system is, for example, a node. The pharmaceutical identification and verification system is connected to the network. The pharmaceutical identification and verification system reads a pharmaceutical name and dosage strength from a container enclosing a pharmaceutical and obtains a detected spectral signature that includes a spectral signature of the pharmaceutical and a spectral signature of the container. The server is connected to the network and the server database. The server receives the pharmaceutical name and dosage strength and the detected spectral signature from the pharmaceutical identification and verification system, compares the detected spectral signature to one or more known spectral signatures in the server database to determine an identity of the pharmaceutical, compares a known pharmaceutical name and dosage strength corresponding to a known spectral signature of a known pharmaceutical that matches the detected spectral signature to the pharmaceutical name and dosage strength to verify the pharmaceutical, and sends a result of the verification to the pharmaceutical identification and verification system. Each of the one or more known spectral signatures in the server database includes a spectral signature of a known pharmaceutical and a spectral signature of a known container.

Another embodiment of the present invention is a method for communicating pharmaceutical verification information between a server and a node where the spectral signature database information and verification transaction information is centrally stored and analyzed by the server and the spectral signature database information includes information about a pharmaceutical container. A node is a pharmaceutical identification and verification system, for example. The node reads a pharmaceutical name and dosage strength from a container enclosing a pharmaceutical. The node is connected to a network and includes a static multimode multiplex spectrometer. The node obtains a detected spectral signature that includes a spectral signature of the pharmaceutical and a spectral signature of the container. The server receives the pharmaceutical name and dosage strength and the detected spectral signature from the pharmaceutical identification and verification system. The server is connected to the network and a server database. The server compares the detected spectral signature to one or more known spectral signatures in the server database to determine an identity of the pharmaceutical. Each of the one or more known spectral signatures includes a spectral signature of a known pharmaceutical and a spectral signature of a known container. The server compares a known pharmaceutical name and dosage strength corresponding to a known spectral signature of a known pharmaceutical that matches the detected spectral signature to the pharmaceutical name and dosage strength to verify the pharmaceutical. The server sends a result of the verification to the node.

Another embodiment of the present invention is a method for distributing pharmaceutical verification information from a central server of a data provider to a pharmaceutical identification and verification system at a customer's location. The pharmaceutical verification information is downloaded from the central server to a portable media device. The portable media device is sent to the customer's location. The pharmaceutical verification information is uploaded from the portable media device to the pharmaceutical identification and verification system.

Figure 1:
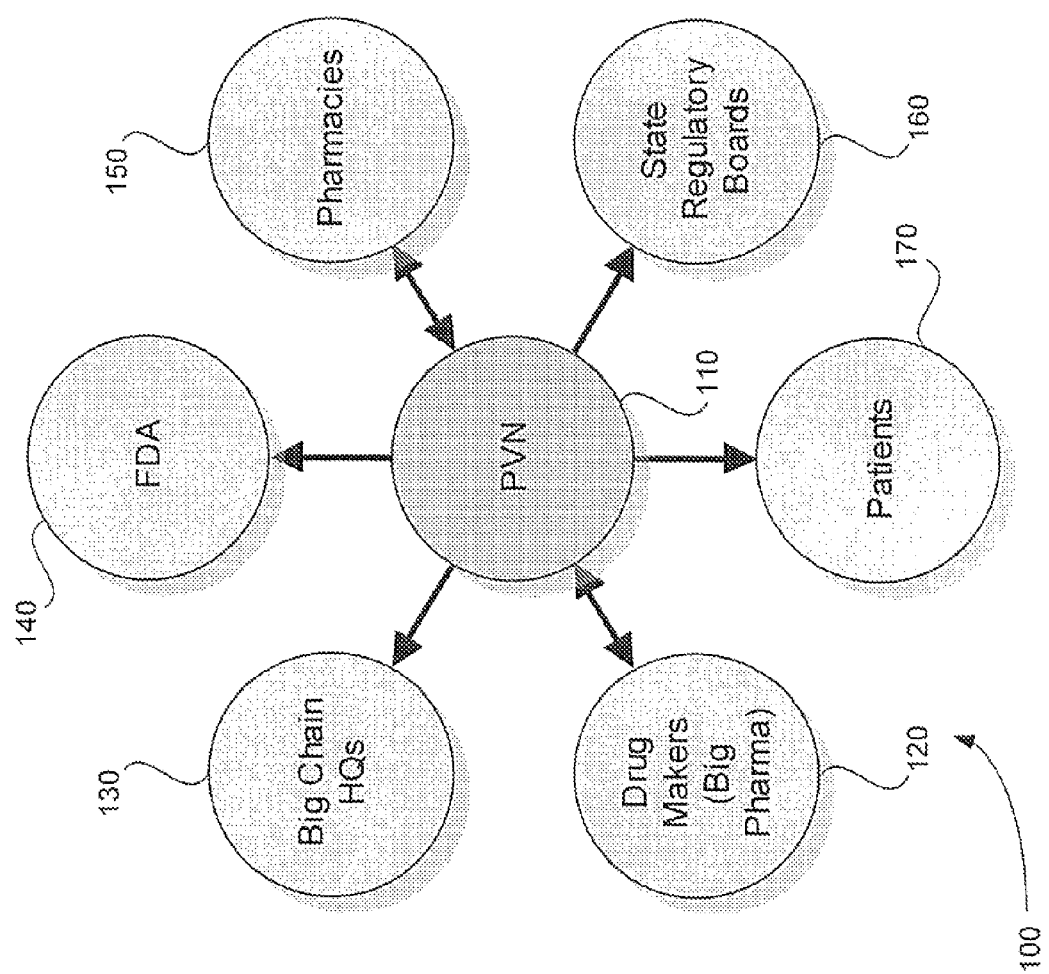
FIG. 1 is a schematic diagram showing a system that lists stakeholders in pharmaceutical verification network, in accordance with an embodiment of the present invention.

Before one or more embodiments of the invention are described in detail, one skilled in the art will appreciate that the invention is not limited in its application to the details of construction, the arrangements of components, and the arrangement of steps set forth in the following detailed description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE INVENTION

An automatic prescription verification system that uses spectroscopic analysis is described in the '923 application uses a static multimode multiplex spectrometer (MMS). A static MMS is described in the '101 patent. A two-dimensional (2D) coded aperture static MMS is described in the '546 application.

According to a system of the '923 application, a standard prescription bottle or vial containing a pharmaceutical of a prescription is placed in the spectroscopic sensor system. The spectroscopic sensor system excites the Raman-active modes of the pharmaceutical and detects the resulting Raman emission. A spectral signature that is derived from the measurement is compared to one or more spectral signatures of known pharmaceuticals that are stored in a database. If the spectral signature of the pharmaceutical in the vial matches a spectral signature of a known pharmaceutical stored in the database, the pharmaceutical in the vial is identified. If the identity of the pharmaceutical in the vial matches the pharmaceutical of the prescription, the prescription is verified.

In order for the system of the '923 application to be able to verify a large number of prescriptions, the database of the system needs to contain a large number of spectral signatures of known pharmaceuticals.

FIG. 1 is a schematic diagram showing a system 100 that lists stakeholders in pharmaceutical verification network (PVN) 110, in accordance with an embodiment of the present invention. The stakeholders of system 100 include drug manufacturers 120, headquarters of large pharmacy chains 130, the Food and Drug Administration (FDA) 140, pharmacies 150, state regulatory boards 160, and patients 170.

In system 100, drug manufacturers 120 get data and statistics from PVN 110. Data from PVN 110 provides drug manufacturers 120 with real-time feedback on drug quality and consistency at the retail level. Drug manufacturers 120 also use this data to reduce counterfeiting of their drugs by detecting counterfeit pharmaceuticals at the retail level. Data from PVN 110 is provided to drug manufacturers 120 as a subscription data service, for example.

Headquarters of large pharmacy chains 130 also get data and statistics from PVN 110. PVN 110 provides headquarters of large pharmacy chains 130 with a centralized means to monitor and assure quality across their chains. PVN also provides headquarters of large pharmacy chains 130 with cost savings, including a reduction in liability insurance.

PVN 110 gives FDA 140 national level visibility on drug quality and counterfeiting, FDA 140, in turn, provides PVN 110 information on new drug releases.

PVN 110 provides pharmacies 150 with retail store level quality assurance. PVN also provides cost savings by speeding the verification process. PVN 110 provides information to pharmacies 150 as a subscription service, for example.

Figure 2:
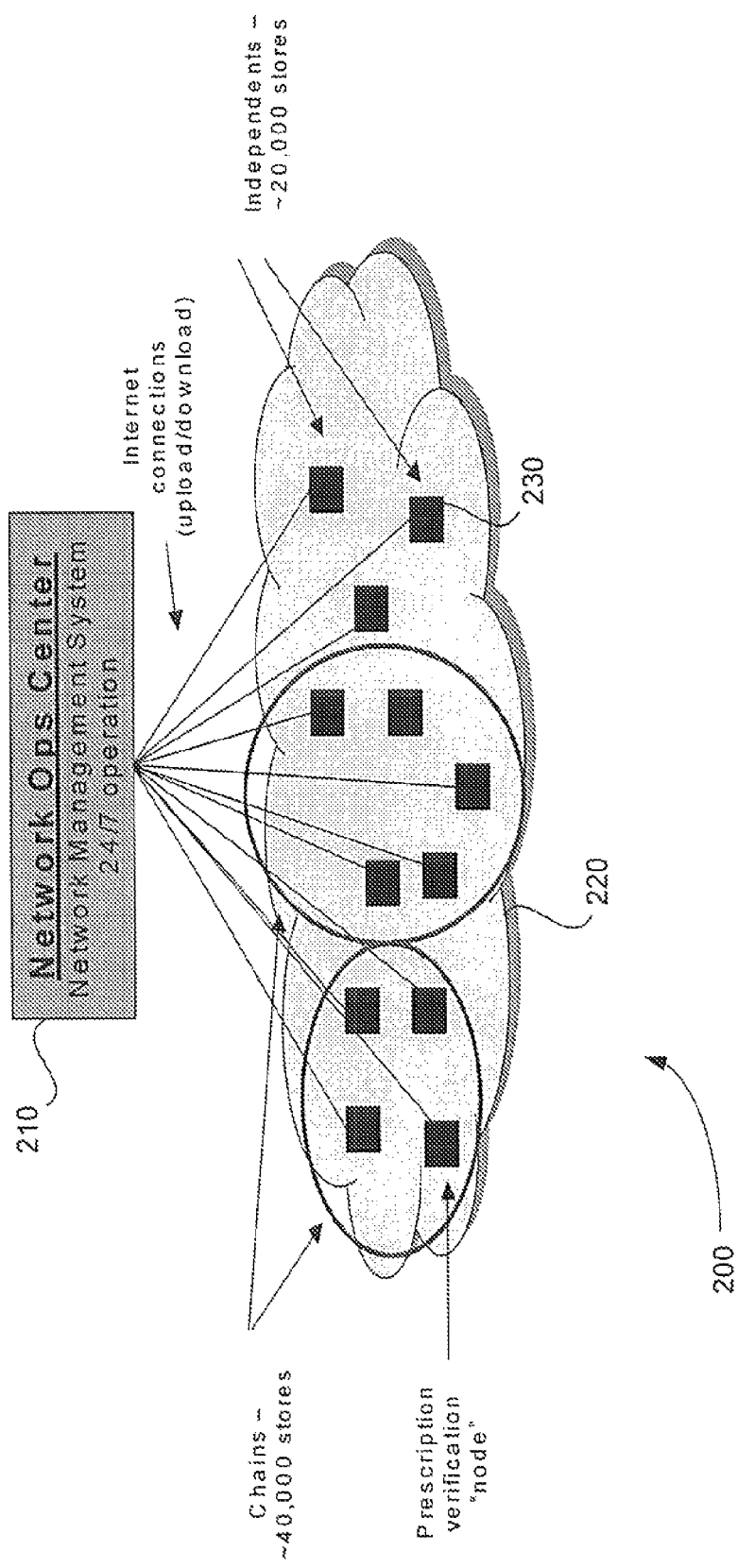
FIG. 2 is a schematic diagram of a pharmaceutical verification network, in accordance with an embodiment of the present invention.

State regulatory boards 160 get state level data and statistics from PVN 110. These state level data and statistics allow state regulatory boards 160 to monitor quality assurance at the state level. Finally, patients 170 are assured of a higher level of verification when PVN 110 is used FIG. 2 is a schematic diagram of a PVN 200, in accordance with an embodiment of the present invention. PVN 200 includes central operations center 210, network 220, and nodes 230. PVN 200 is a branded managed service network capable of monitoring and assuring pharmacy quality assurance worldwide, nationwide, state-wide, or across a chain of pharmacies. Central operations center 210 manages a network of nodes 230 for near real-time drug database maintenance, data collection, sharing, data mining, and alarm monitoring. Central operations center 210 is coupled to nodes 230 through network 220. Network 220 is the Internet, for example. Central operations center 210 includes a network management system (NMS) with 24 hour and seven days a week operation.

PVN 200 provides drug database maintenance, counterfeit pharmaceutical tracking, statistics by store, chain, or geography, diagnostics to trigger field service or repair, and alarm monitoring of failures and exceptions. PVN 200 can reduce verification costs by lower liability insurance. PVN 200 is provided to customers for a monthly service fee, for example. In another embodiment of the present invention, PVN 200 is provided to customers using a pay per use model.

At least one pharmaceutical identification and verification system is available at each node 230. One or more nodes 230 are located at locations that include, but are not limited to, chain store pharmacies, independent pharmacies, or hospitals. A pharmaceutical identification and verification system is provided to a node 230 as part of the subscription to PVN 200, for example. In another embodiment of the present invention, a pharmaceutical identification and verification system is purchased separately and in addition to a subscription by a node 230.

Figure 3:
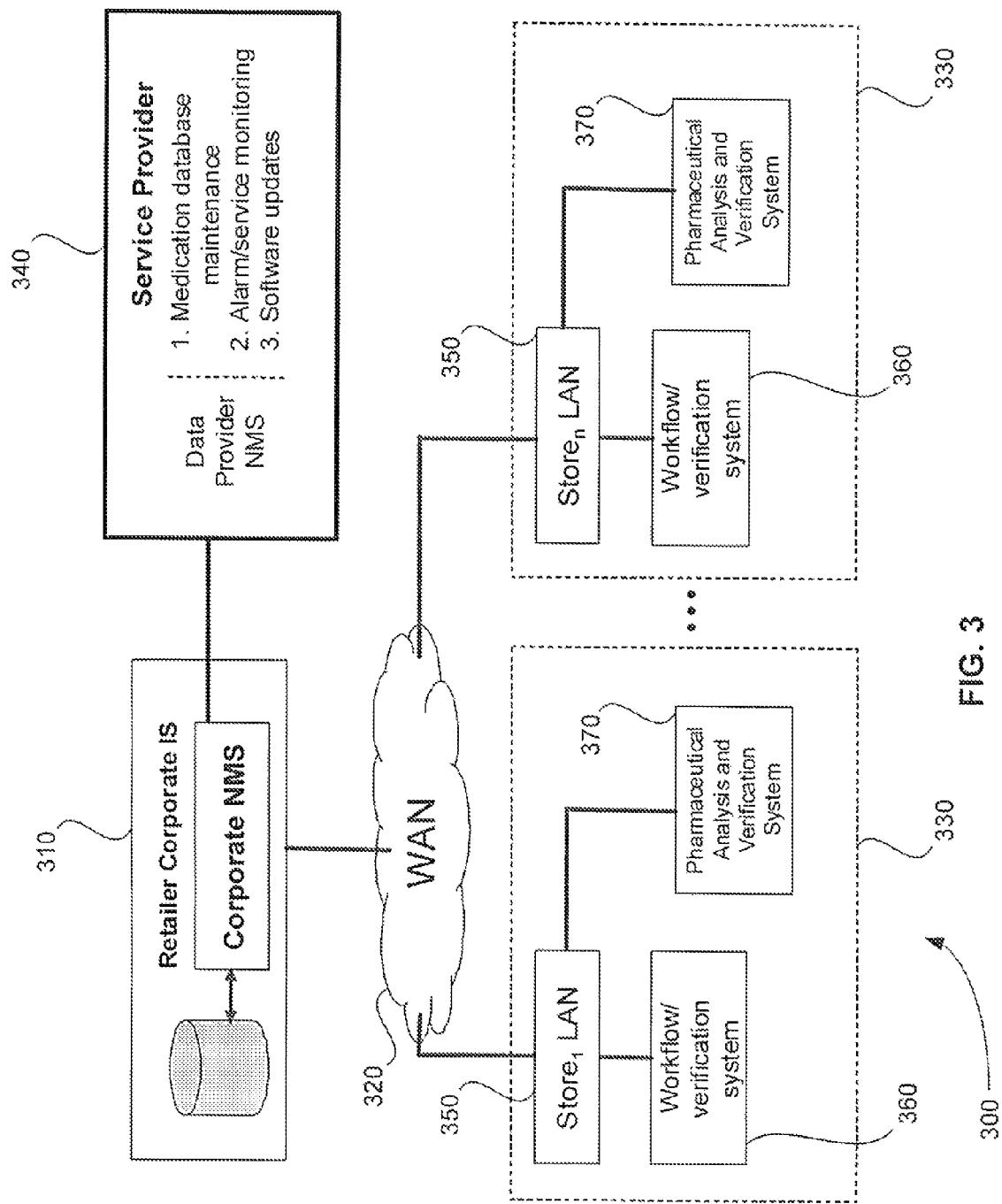
FIG. 3 is a schematic diagram of a pharmaceutical verification network that includes local area networks at each node, in accordance with an embodiment of the present invention.

FIG. 3 is a schematic diagram of a PVN 300 that includes local area networks 350 at each node 330, in accordance with an embodiment of the present invention. PVN 300 includes central operations center 310, network 320, nodes 330, and data provider 340. Central operations center 310 monitors and provides pharmacy quality assurance for nodes 330. Central operations center 310 is the corporate information systems department of a chain pharmacy retailer, for example.

Data provider 340 is coupled to central operations center 310. Data provider 340 is coupled to central operations center 310 using an NMS, for example. Data provider 340 provides central operations center 310 with medication database maintenance, alarm and service monitoring, and software updates.

Central operations center 310 is also coupled one or more nodes 330 through network 320. Network 330 is a wide area network (WAN), for example. Nodes 330 include local area network 350, workflow and verification system 360, and pharmaceutical analysis and verification system 370. Workflow and verification system 360 and pharmaceutical analysis and verification system 370 are coupled through local area network 350. Local area network is coupled to network 320.

Pharmaceutical analysis and verification system 370 is a spectrometric system used to obtain a spectral signal of a pharmaceutical compound, for example. Software updates for pharmaceutical analysis and verification system 370 are sent from data provider 340 through central operations center 310, for example.

Workflow and verification system 360 is a computer-based system for comparing the spectral signal to information obtained for a prescription written for the pharmaceutical compound, for example. Medication database updates for workflow and verification system 360 are sent from data provider 340 through central operations center 310, for example.

Figure 4:
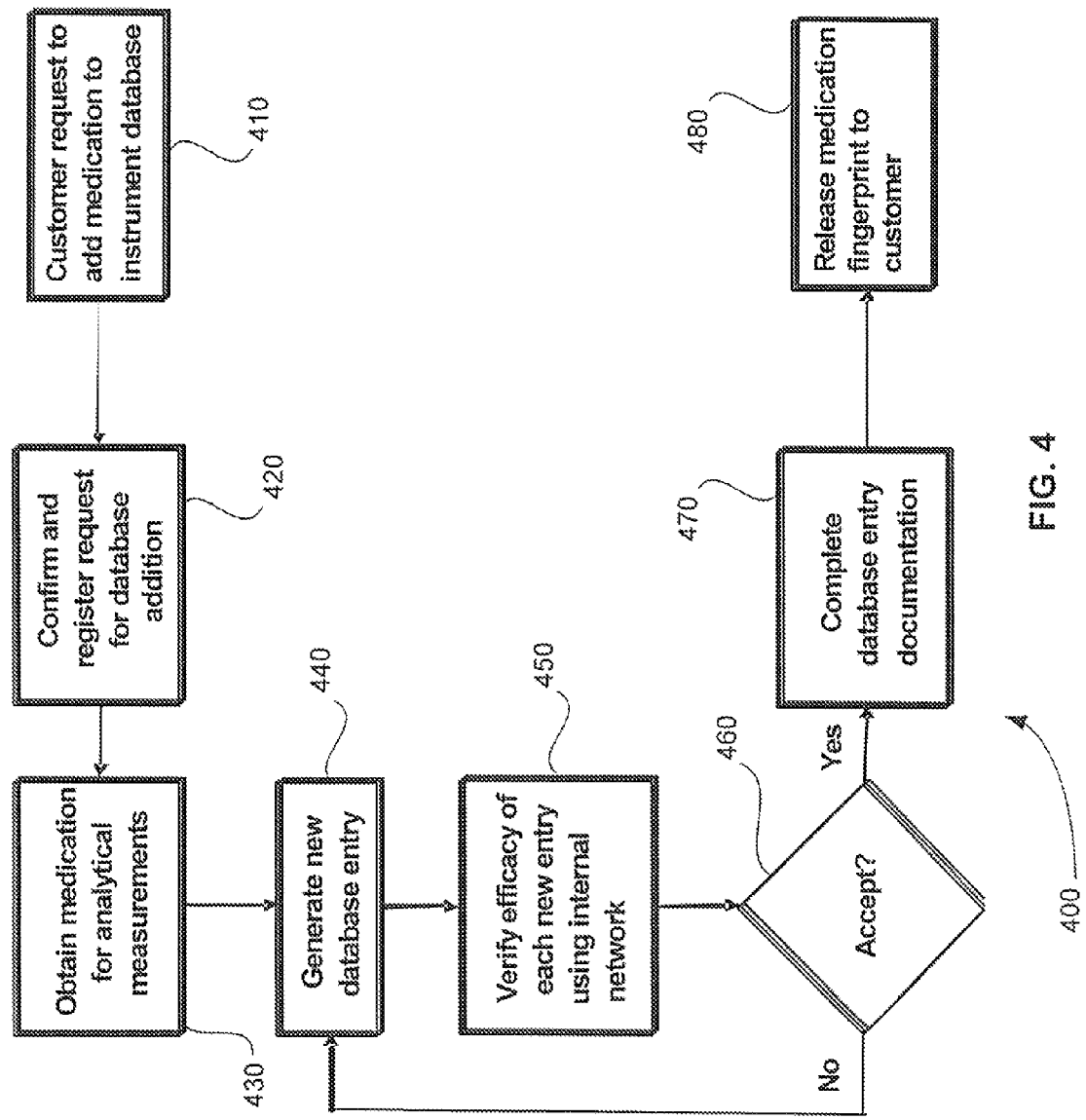
FIG. 4 is a flowchart showing a method of generating, testing, and releasing new medication fingerprints.

FIG. 4 is a flowchart showing a method 400 of generating, testing, and releasing new medication fingerprints. A medication fingerprint for a spectrometric pharmaceutical analysis and verification system is a spectral signature, for example.

In step 410 of method 400, a customer requests to add a medication to an instrument database. The customer is a customer of a PVN and the request is made to a data provider of the PVN, for example.

In step 420, the data provider confirms the request and registers the request for database addition.

In stem 430, the data provider obtains the medication for analytical measurements. The data provider for a spectrometric system obtains the medication for a spectral analysis, for example.

In step 440, the data provider generates a new fingerprint or database entry. The new database entry for a spectrometric system is a spectral signature, for example.

In step 450, the data provider verifies the efficacy of each new database entry using an internal network.

In step 460, the data provider makes a decision on whether or not to accept the new database entry. If the new entry is not accepted, the process returns to step 440. If the new database entry is accepted, step 470 is executed.

In step 470, the data provider completes documentation of the new database entry.

In step 480, the new database entry is released to the customer.

A system for performing method 400 is referred to as a medication database laboratory (MDL), for example. An MDL ensures accurate medication identifications and no false positives. An MDL adds and deletes medication database entries. An MDL monitors for counterfeit pharmaceuticals. Through its iterative process an MDL drives continuous improvement oft the medication verification process.

Figure 5:
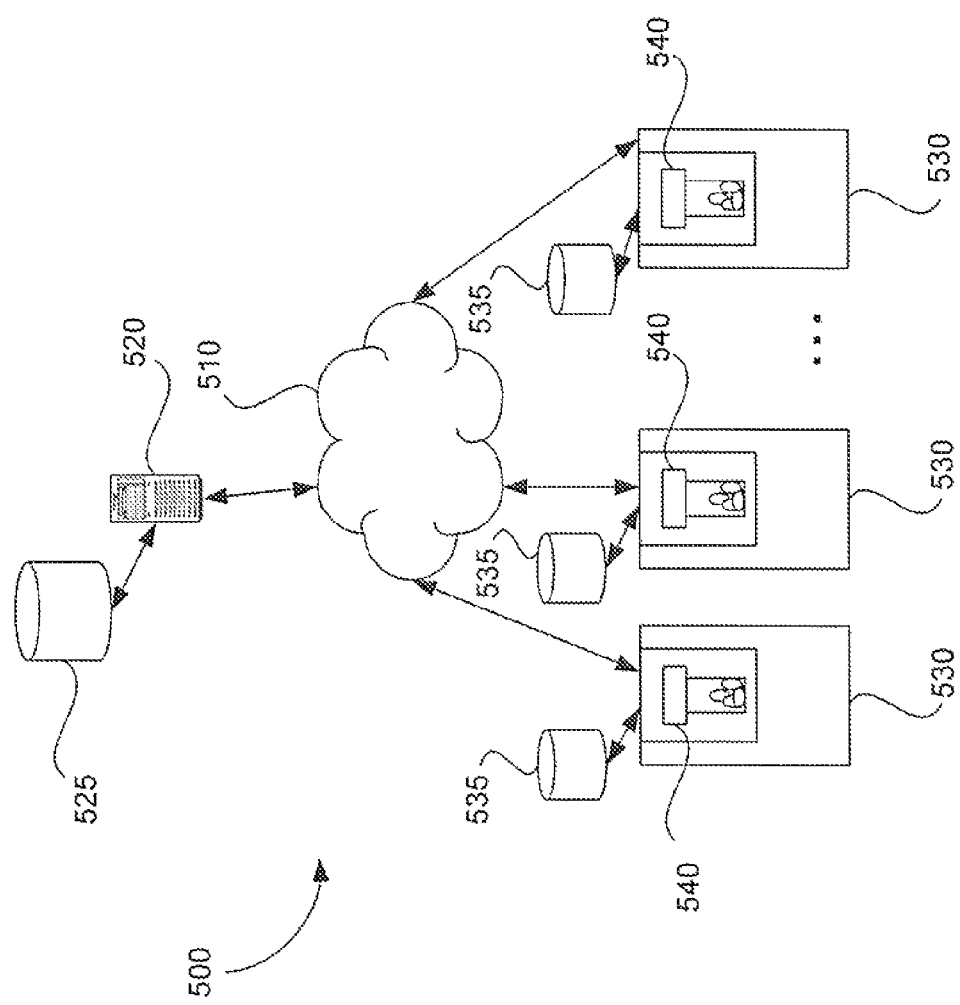
FIG. 5 is a schematic diagram of a system for communicating pharmaceutical verification information where the spectral signature database information and verification transaction information is stored at each node and a node includes a static multimode multiplex spectrometer, in accordance with an embodiment of the present invention.

FIG. 5 is a schematic diagram of a system 500 for communicating pharmaceutical verification information where the spectral signature database information and verification transaction information is stored at each node and a node includes a static MMS, in accordance with an embodiment of the present invention. System 500 includes network 510, server 520, server database 525, one or more pharmaceutical identification and verification systems 530, and one or more client databases 535. Network 510 is, for example, the Internet. A node, for example, includes at least one pharmaceutical identification and verification system 530.

Server 520 is a centralized location for gathering, storing and disseminating pharmaceutical verification transaction information. One skilled in the art can appreciate that server 520 can include one or more physical computers and one or more server databases 525. Server 520 is coupled to network 510 and server database 525. Server 520 stores at least one known spectral signature of a known pharmaceutical and a corresponding known pharmaceutical name and dosage strength of the known pharmaceutical in server database 525. In another embodiment of system 500, server 520 stores at least one known spectral signature of a known pharmaceutical produced by an MMS in server database 525.

At least one pharmaceutical identification and verification system 530 is also coupled to network 510. Pharmaceutical identification and verification system 530 is, for example, a spectrometric system. In the preferred embodiment of the present invention, pharmaceutical identification and verification system 530 includes an MMS as described in the '923 application.

Pharmaceutical identification and verification system 530 receives at least one known spectral signature and the corresponding known pharmaceutical name and dosage strength from server 520. Pharmaceutical identification and verification system 530 is coupled to client database 535. Pharmaceutical identification and verification system 530 stores at least one known spectral signature and the corresponding known pharmaceutical name and dosage strength in client database 535.

Pharmaceutical identification and verification system 530 reads a pharmaceutical name and dosage strength from container 540 enclosing a pharmaceutical. Container 540 can be, but is not limited to, a manufacturer's bottle, a wholesaler's bottle, or a prescription vial. The pharmaceutical name and dosage strength is read from a label on container 540, for example. The label read on a prescription vial is a prescription label, for example. Pharmaceutical identification and verification system 530 obtains or detects a spectral signature for the pharmaceutical. In another embodiment of system 500, the detected spectral signature is produced by an MMS. Pharmaceutical identification and verification system 530 compares the detected spectral signature to the known spectral signatures in local database 535 to verify the identity of the pharmaceutical.

The detected and known spectral signatures can include traditional wavelength versus intensity information and the direct digital data recorded from a detector of a pharmaceutical identification and verification system. The detected and the known spectral signatures can also include mathematical derivatives of either or both sources of data. Local database 535 can contain a national drug code (NDC) and/or the name of the drug and the dosage level. In addition, local database 535 can be frequently updated to include new pharmaceuticals, generic formulations, and each new dosage variant.

Pharmaceutical identification and verification system 530 preferably sends a packet of transaction information to server 520 each time the verification system 530 verifies a pharmaceutical or detects a spectral signature. This transaction information can contain the spectral signature, the verification results, and validation information regarding the performance of verification system 530. Server 520 records this transaction information in server database 525. Users of pharmaceutical identification and verification system 530 can include, but are not limited to, pharmacies, drug wholesalers, hospitals, nursing homes, drug companies, and companies providing verification services.

If pharmaceutical identification and verification system 530 cannot match the obtained spectral signature to a known spectral signature in client database 535, either the pharmaceutical's spectral signature was not included in client database 535, no drug is present in container 540, the wrong drug was dispensed into container 540, or the pharmaceutical is a counterfeit. In all cases, pharmaceutical identification and verification system 530 sends the spectral signature and the corresponding pharmaceutical name and dosage strength to server 520 for analysis as a non-database entry pharmaceutical, improperly filled prescription, or possibly a counterfeit drug.

If the spectral signature obtained by pharmaceutical identification and verification system 530 matches a known spectral signature stored in client database 535 of pharmaceutical identification and verification system 530, pharmaceutical identification and verification system 530 compares the pharmaceutical name and dosage strength to the known pharmaceutical name and dosage strength in client database 535 to verify the prescription. If the names and strengths match, the pharmaceutical is verified and the results and transaction information are transferred to server 520. If the names and strengths do not match, the pharmaceutical is not verified and the results and transaction information are transferred to server 520.

Periodically server 520 sends pharmaceutical identification and verification system 530 an update to the spectral signature database when new spectral signatures and the corresponding pharmaceutical information are available. Server 520 obtains new and updated spectral signatures from a data provider, such as an MDL (not shown in FIG. 1).

In another embodiment of system 500, pharmaceutical identification and verification system 530 is able to analyze a pharmaceutical without opening container 540. In other words, pharmaceutical identification and verification system 530 performs an analysis of the pharmaceutical through the container. As a result, a detected spectral signature of a pharmaceutical analyzed by pharmaceutical identification and verification system 530 without opening container 540 also includes a spectral signature of container 540. In order to compare this detected spectral signal to a known spectral signal, a known spectral signature received from server 520 also includes a spectral signature of a known container. A container includes the container's closure (e.g. lid, top, or cap).

Figure 6:
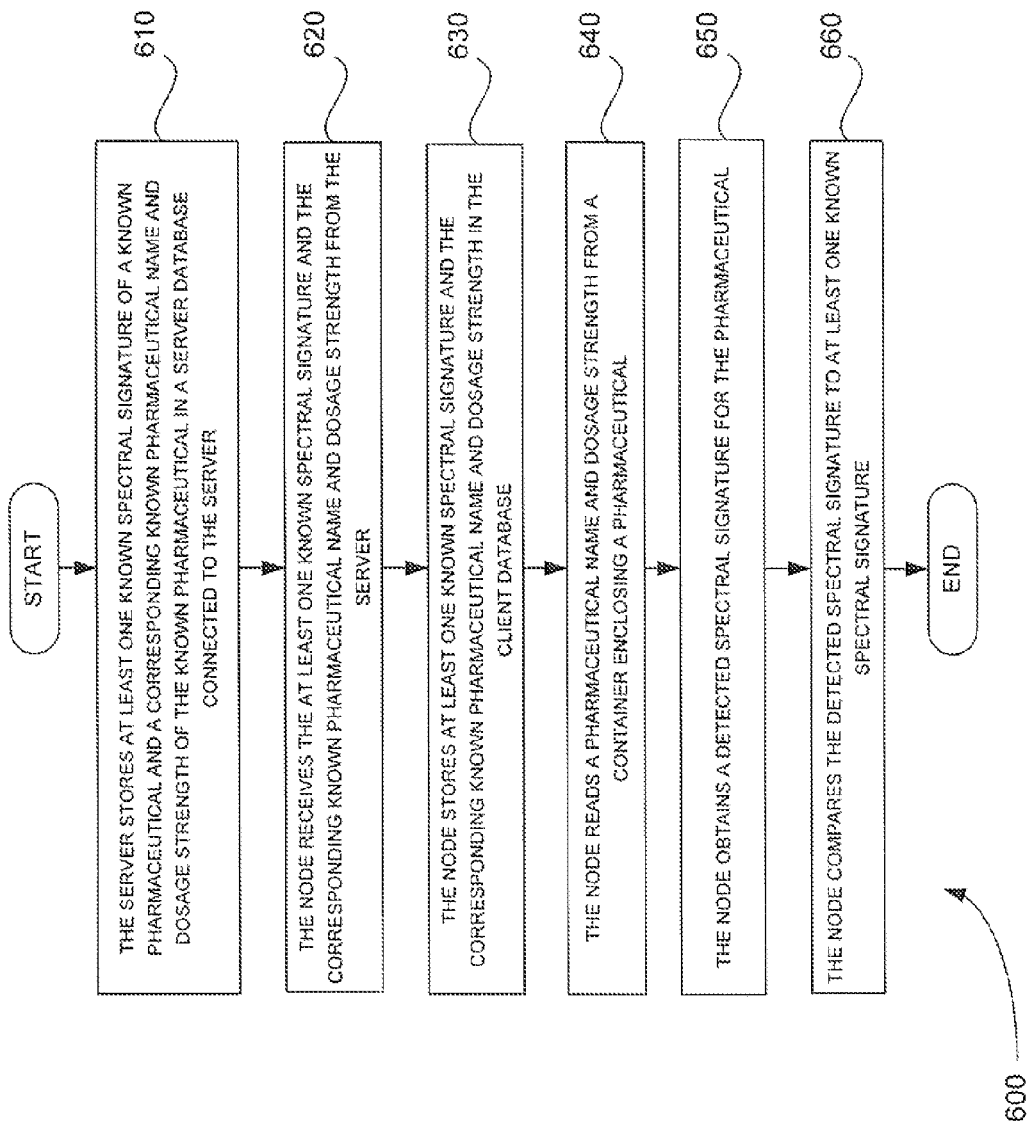
FIG. 6 is a flowchart showing a method for communicating pharmaceutical verification between a server and a node where the spectral signature database information and verification transaction information is stored at each node and a node includes a static multimode multiplex spectrometer, in accordance with an embodiment of the present invention.

FIG. 6 is a flowchart showing a method 600 for communicating pharmaceutical verification information between a server and a node where the spectral signature database information and verification transaction information is stored at each node and a node includes a static multimode multiplex spectrometer, in accordance with an embodiment of the present invention. A node is pharmaceutical identification and verification system, for example.

In step 610 of method 600, the server stores at least one known spectral signature of a known pharmaceutical and a corresponding known pharmaceutical name and dosage strength of the known pharmaceutical in a server database connected to the server. The server is connected to a network.

In step 620, the node receives the at least one known spectral signature and the corresponding known pharmaceutical name and dosage strength from the server. The node is connected to the network and a client database.

In step 630, the node stores at least one known spectral signature and the corresponding known pharmaceutical name and dosage strength in the client database.

In step 640, the node reads a pharmaceutical name and dosage strength from a container enclosing a pharmaceutical.

In step 650, the node obtains a detected spectral signature for the pharmaceutical.

In step 660, the node compares the detected spectral signature to at least one known spectral signature.

In another embodiment of method 600, the at least one known spectral signature received by the node from the server includes a spectral signature of a known container and the detected spectral signature obtained by the node includes a spectral signature of the container. In another embodiment of method 600, the at least one known spectral signature received by the node from the server is produced by a static multimode multiplex spectrometer used by the server and the detected spectral signature is produced by the static multimode multiplex spectrometer of the node.

Figure 7:
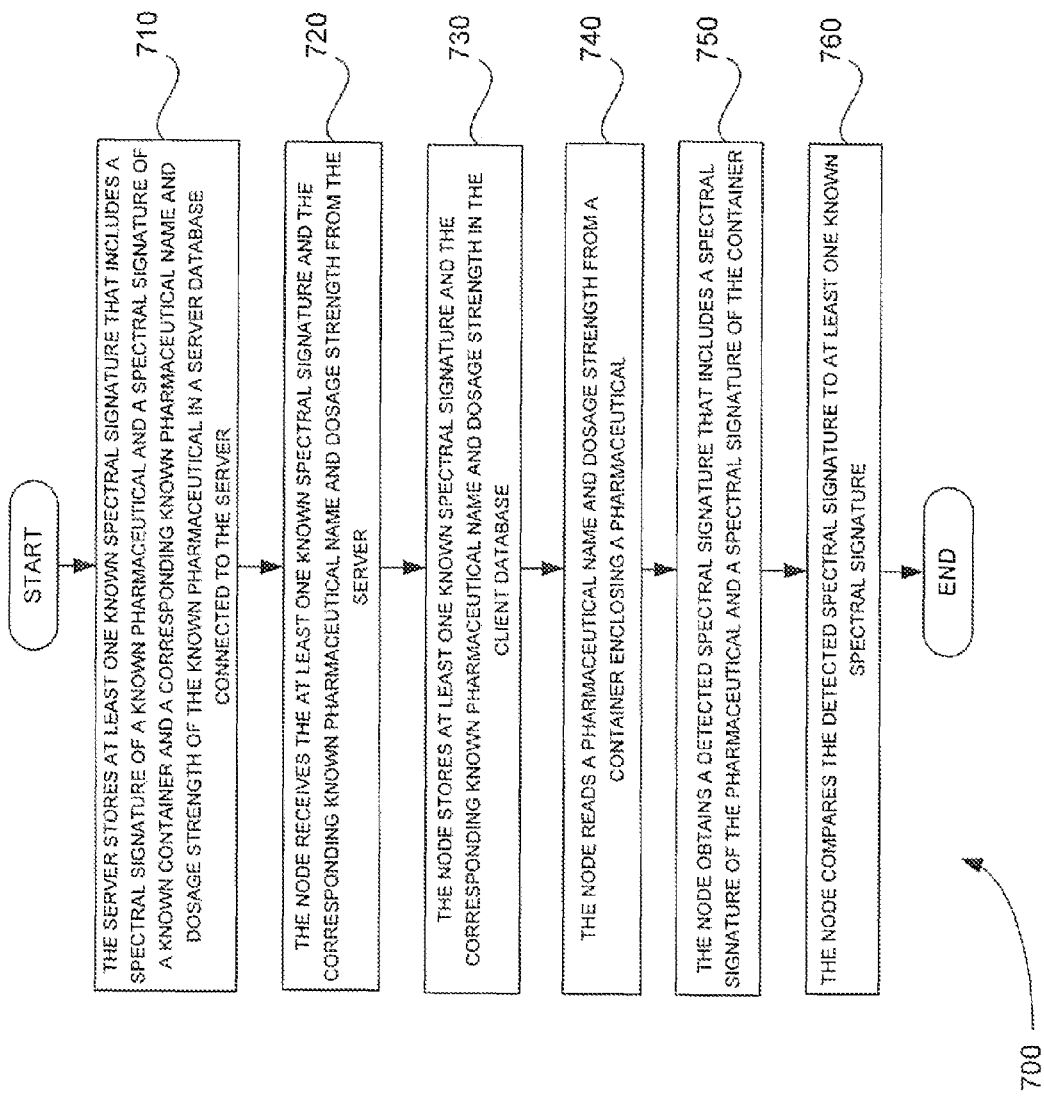
FIG. 7 is a flowchart showing a method for communicating pharmaceutical verification information between a server and a node where the spectral signature database information and verification transaction information is stores at each node and the spectral signature database information includes information about a pharmaceutical container, in accordance with an embodiment of the present invention.

FIG. 7 is a flowchart showing a method 700 for communicating pharmaceutical verification information between a server and a node where the spectral signature database information and verification transaction information is stored at each node and the spectral signature database information includes information about a pharmaceutical container, in accordance with an embodiment of the present invention. A node is a pharmaceutical identification and verification system, for example.

In step 710 of method 700, the server stores at least one known spectral signature that includes a spectral signature of a known pharmaceutical and a spectral signature of a known container and a corresponding known pharmaceutical name and dosage strength of the known pharmaceutical in a server database connected to the server. The server is connected to a network.

In step 720, the node receives the at least one known spectral signature and the corresponding known pharmaceutical name and dosage strength from the server. The node is connected to the network and a client database.

In step 730, the node stores at least one known spectral signature and the corresponding known pharmaceutical name and dosage strength in the client database.

In step 740, the node reads a pharmaceutical name and dosage strength from a container enclosing a pharmaceutical.

In step 750, the node obtains a detected spectral signature that includes a spectral signature of the pharmaceutical and a spectral signature of the container.

In step 760, the node compares the detected spectral signature to at least one known spectral signature.

Figure 8:
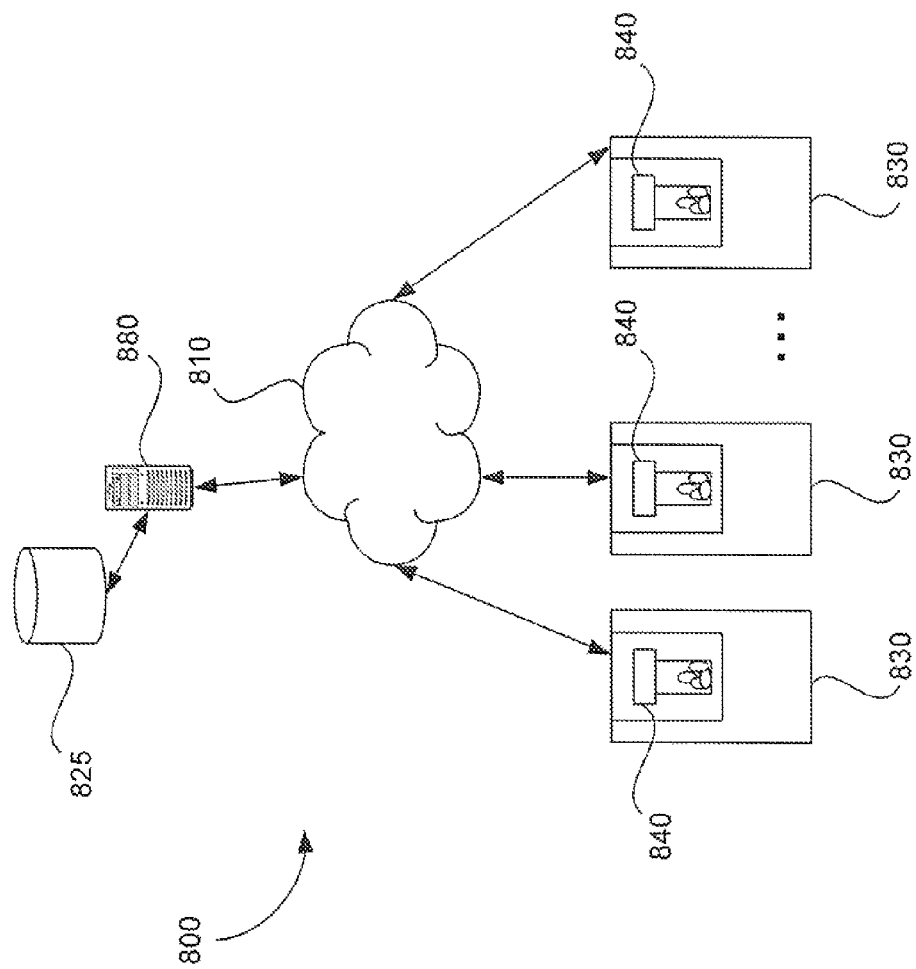
FIG. 8 is a schematic diagram of a system for communicating pharmaceutical verification information where the spectral signature database information and verification transaction information is centrally stored and analyzed and a node includes a static multimode multiplex spectrometer, in accordance with an embodiment of the present invention.

FIG. 8 is a schematic diagram of a system 800 for communicating pharmaceutical verification information where the spectral signature database information and verification transaction information is centrally stored and analyzed and a node includes a static multimode multiplex spectrometer, in accordance with an embodiment of the present invention. A node, for example, includes at least one pharmaceutical identification and verification system 830. System 800 includes network 810, server 820, server database 825, and one or more pharmaceutical identification and verification systems 830. Network 810 is, for example, the Internet.

Pharmaceutical identification and verification system 830 is coupled to network 810. Pharmaceutical identification and verification system 830 preferably includes a static MMS. Pharmaceutical identification and verification system 830 reads a pharmaceutical name and dosage strength from container 840 enclosing a pharmaceutical and obtains a detected spectral signature for the pharmaceutical. Container 840 can be, but is not limited to, a manufacturer's bottle, a wholesaler's bottle, or a prescription vial.

In another embodiment of the system 830, the detected spectral signature includes a spectral signature of the pharmaceutical and a spectral signature of container 840.

In another embodiment of the system 830, the detected spectral signature is produced by the MMS. Server 820 and server database 825 are a centralized location for gathering, storing, and disseminating pharmaceutical verification transaction information. One skilled in the art can appreciate that server 820 can include one or more physical computers and one or more server databases 825. Server 820 is coupled to network 810 and server database 825. Server 820 receives the pharmaceutical name and dosage strength from container 840 prior to container 840 being inserted into pharmaceutical identification and verification system 830. Server 820 compares the detected spectral signature received from pharmaceutical identification and verification system 830 to one or more known spectral signatures in server database 825 to determine the identity of the pharmaceutical.

In another embodiment of system 800, each of the one or more known spectral signatures in server database 825 includes a spectral signature of a known pharmaceutical and a spectral signature of a known container. Server 820 compares a known pharmaceutical name and dosage strength corresponding to a known spectral signature that matches the spectral signature sent by pharmaceutical identification and verification system 830 to verify the pharmaceutical. Server 820 sends a result of the verification to pharmaceutical identification and verification system 830 and pharmaceutical identification and verification system 830 displays the result to a user.

Server 820 also stores each spectral signature and the corresponding pharmaceutical name and dosage strength that is not identified or verified. Unidentified spectral signatures are recorded to permit future investigation, possibly leading to the identification of counterfeit pharmaceuticals.

Periodically server 820 receives an update of the spectral signature database when new spectral signatures are available. Server 820 obtains new and updated spectral signatures from a data provider, such as an MDL (not shown in FIG. 8).

Figure 9:
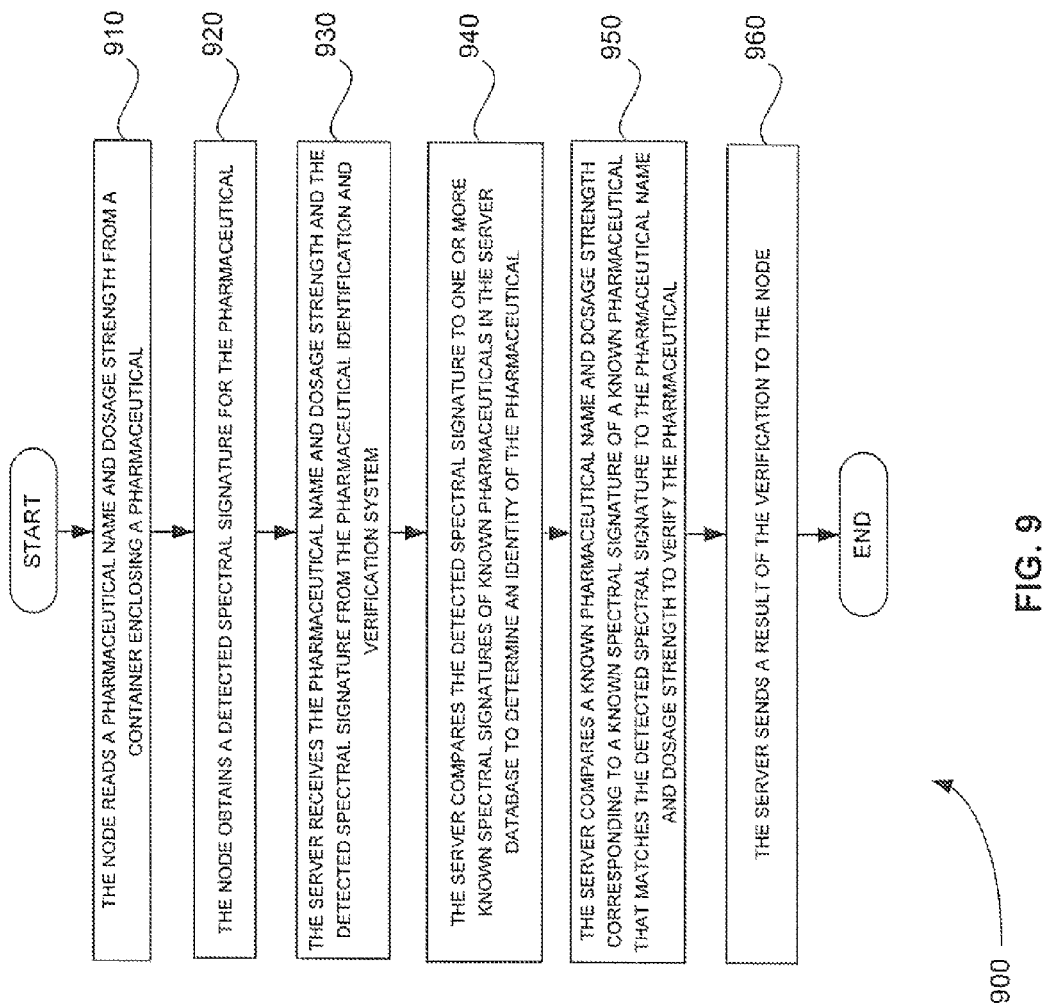
FIG. 9 is a flowchart showing a method for communicating pharmaceutical verification information between a server and a node where the spectral signature database information and verification transaction information is centrally stored and analyzed and a node includes a static multimode multiplex spectrometer, in accordance with an embodiment of the present invention.

FIG. 9 is a flowchart showing a method 900 for communicating pharmaceutical verification information between a server and a node where the spectral signature database information and verification transaction information is centrally stored and analyzed and a node includes a static multimode multiplex spectrometer, in accordance with an embodiment of the present invention. A node is a pharmaceutical identification and verification system, for example.

In step 910 of method 900, the node reads a pharmaceutical name and dosage strength from a container enclosing a pharmaceutical. The node is connected to a network and includes a static multimode multiplex spectrometer.

In step 920, the node obtains a detected spectral signature for the pharmaceutical.

In step 930, the server receives the pharmaceutical name and dosage strength and the detected spectral signature from the pharmaceutical identification and verification system. The server is connected to the network and a server database.

In step 940, the server compares the detected spectral signature to one or more known spectral signatures of known pharmaceuticals in the server database to determine an identity of the pharmaceutical.

In step 950, the server compares a known pharmaceutical name and dosage strength corresponding to a known spectral signature of a known pharmaceutical that matches the detected spectral signature to the pharmaceutical name and dosage strength to verify the pharmaceutical.

In step 960, the server sends a result of the verification to the node.

In another embodiment of method 900, the known spectral signature includes a spectral signature of a known container and the detected spectral signature includes a spectral signature of the container. In another embodiment of method 900, the server records each detected spectral signature that is not verified in the server database.

Figure 10:
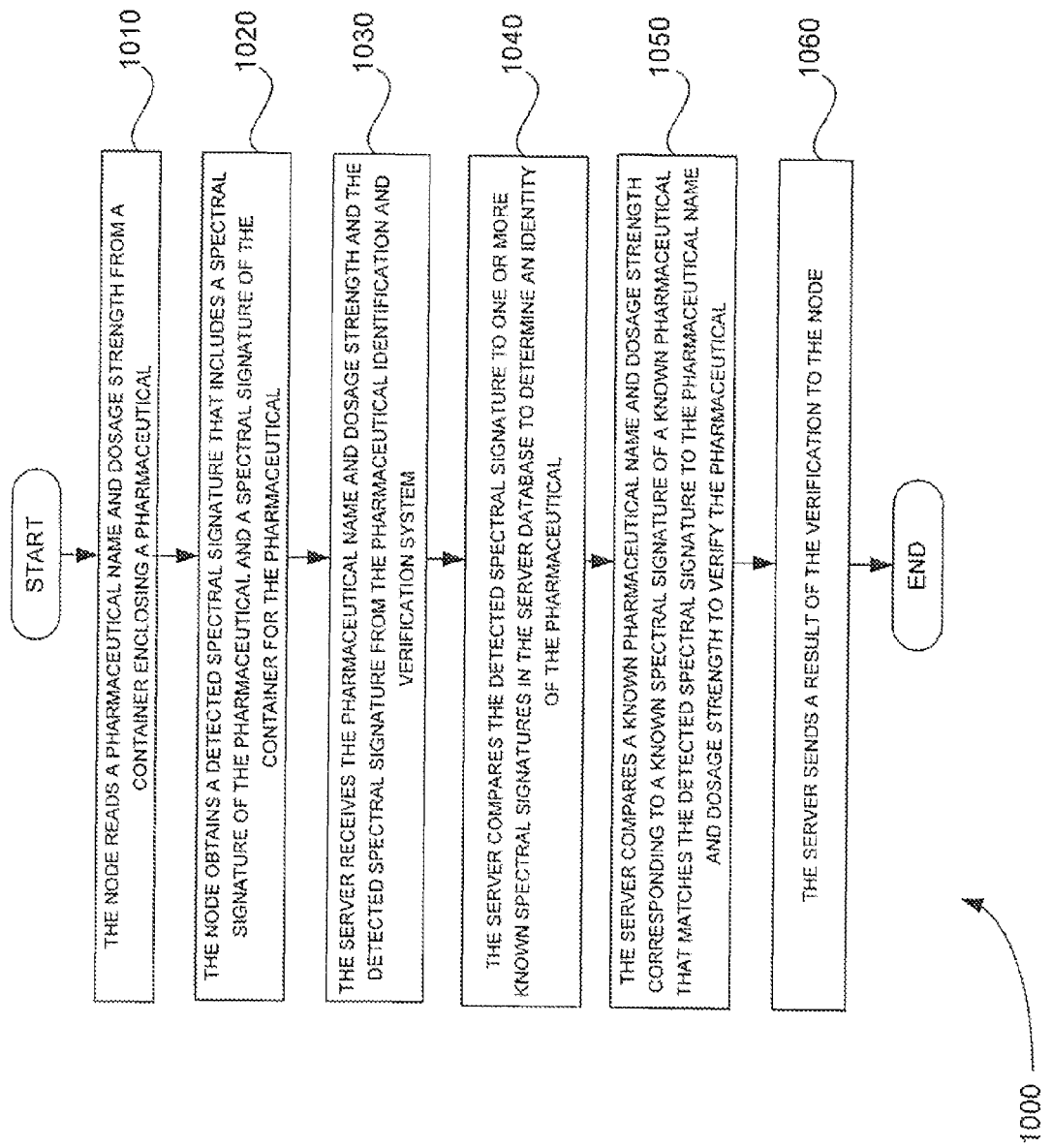
FIG. 10 is a flowchart showing a method for communicating pharmaceutical verification information between a server and a node where the spectral signature database information and verification transaction information is centrally stored and analyzed and the spectral signature database information includes information about a pharmaceutical container, in accordance with an embodiment of the present invention.

FIG. 10 is a flowchart showing a method 1000 for communicating pharmaceutical verification information between a server and a node where the spectral signature database information and verification transaction information is centrally stored and analyzed and the spectral signature database information includes information about a pharmaceutical container, in accordance with an embodiment of the present invention. A node is a pharmaceutical identification and verification system, for example.

In step 1010 of method 1000, the node reads a pharmaceutical name and dosage strength from a container enclosing a pharmaceutical. The node is connected to a network.

In step 1020, the node obtains a detected spectral signature that includes a spectral signature of the pharmaceutical and a spectral signature of the container.

In step 1030, the server receives the pharmaceutical name and dosage strength and the detected spectral signature from the pharmaceutical identification and verification system. The server is connected to the network and a server database.

In step 1040, the server compares the detected spectral signature to one or more known spectral signatures in the server database to determine an identity of the pharmaceutical. Each of the one or more known spectral signatures includes a spectral signature of a known pharmaceutical and a spectral signature of a known container.

In step 1050, the server compares a known pharmaceutical name and dosage strength corresponding to a known spectral signature of a known pharmaceutical that matches the detected spectral signature to the pharmaceutical name and dosage strength to verify the pharmaceutical.

In step 1060, the server sends a result of the verification to the node.

In another embodiment of method 1000, the server records each detected spectral signature that is not verified in the server database.

Figure 11:
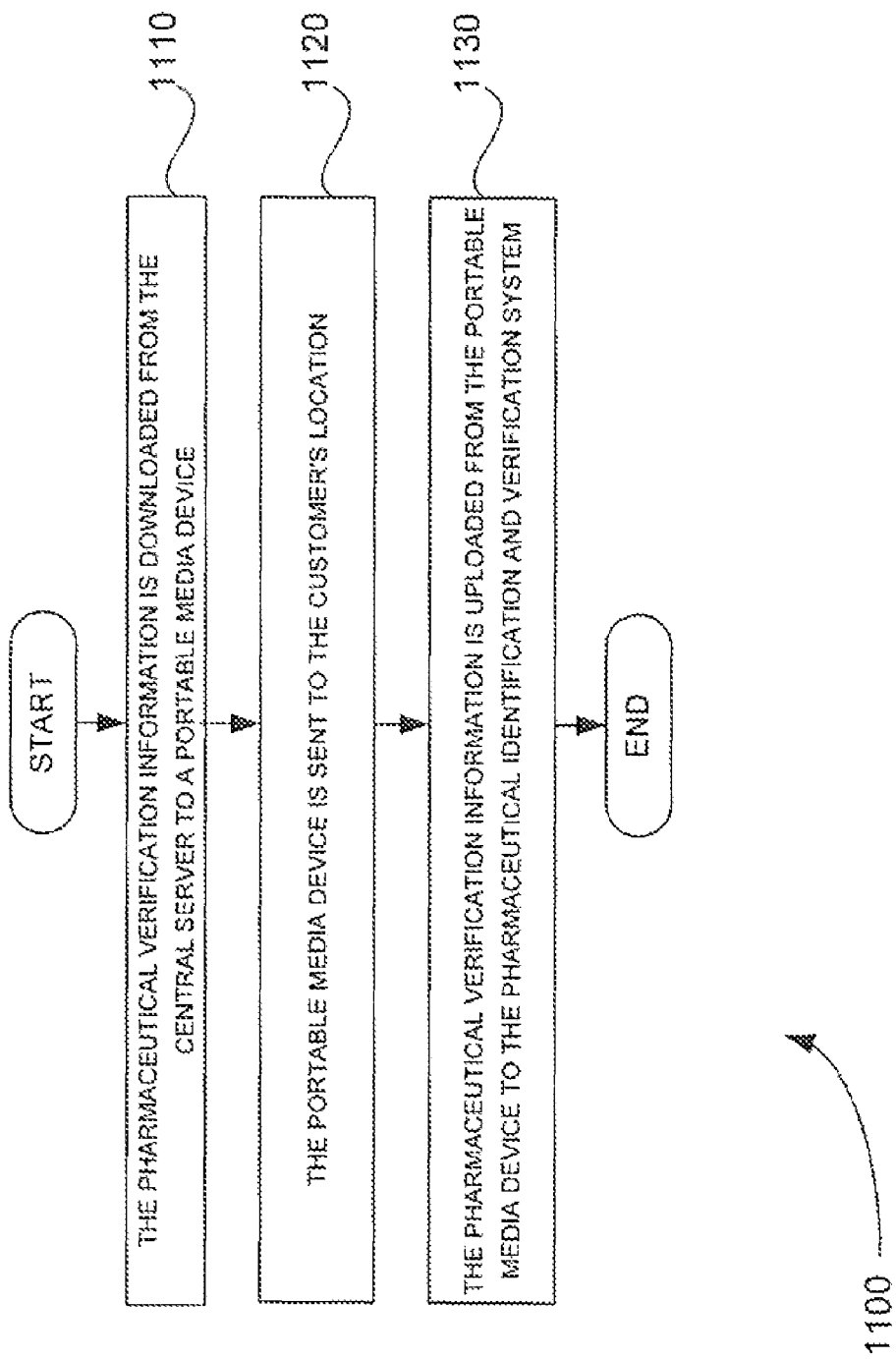
FIG. 11 is a flowchart showing a method for distributing pharmaceutical verification information from a central server of a data provider to a pharmaceutical identification and verification system at a customer's location, in accordance with an embodiment of the present invention.

FIG. 11 is a flowchart showing a method 1100 for distributing pharmaceutical verification information from a central server of a data provider to a pharmaceutical identification and verification system at a customer's location, in accordance with an embodiment of the present invention.

In step 1110 of method 1100, the pharmaceutical verification information is downloaded from the central server to a portable media device. The portable media device can be, but is not limited to, a compact disc read-only memory, a floppy disk, a magnetic tape, a flash memory drive, a flash memory card, a firmware device, a thumb-drive, or a universal serial bus drive.

In step 1120, the portable media device is sent to the customer's location. The portable media device is mailed to the customer's location, for example.

In step 1130, the pharmaceutical verification information is uploaded from the portable media device to the pharmaceutical identification and verification system. The pharmaceutical identification and verification system includes a static MMS, for example.

In another embodiment of method 1110, the pharmaceutical verification information includes at least one known spectral signature of a known pharmaceutical and a corresponding known pharmaceutical name and dosage strength of the known pharmaceutical. In another embodiment of method 1110, the at least one known spectral signature also includes a spectral signature of a known pharmaceutical container. The known pharmaceutical container can include, but is not limited to, a prescription vial, a manufacturer's bottle, and a wholesaler's bottle. In another embodiment of method 1110, the at least one known spectral signal is produced by a static MMS.

As used to describe embodiments of the present invention, the term "coupled" encompasses a direct connection, an indirect connection, or a combination thereof. Two devices that are coupled can engage in direct communications, in indirect communications, or a combination thereof. Moreover, two devices that are coupled need not be in continuous communication, but can be in communication typically, periodically, intermittently, sporadically, occasionally, and so on. Further, the term "communication" is not limited to direct communication, but also includes indirect communication.

Embodiments of the present invention relate to data communications using one or more networks. The data communications can be carried by one or more communications channels of the one or more networks. A network can include wired communication links (e.g., coaxial cable, copper wires, optical fibers, a combination thereof, and so on), wireless communication links (e.g., satellite communication links, terrestrial wireless communication links, satellite-to-terrestrial communication links, a combination thereof, and so on), or a combination thereof. A communications link can include one or more communications channels, where a communications channel carries communications. For example, a communications link can include multiplexed communications channels, such as time division multiplexing ("TDM") channels, frequency division multiplexing ("FDM") channels, code division multiplexing ("CDM") channels, wave division multiplexing ("WDM") channels, a combination thereof, and so on.

In accordance with an embodiment of the present invention, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed. The terms "instructions configured to be executed" and "instructions to be executed" are meant to encompass any instructions that are ready to be executed in their present form (e.g., machine code) by a processor, or require further manipulation (e.g., compilation, decryption, or provided with an access code, etc.) to be ready to be executed by a processor.

Systems and methods in accordance with an embodiment of the present invention disclosed herein can advantageously provide feedback on drug quality and consistency at the retail pharmacy level. These systems and methods can also identify and reduce drug counterfeiting.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for communicating pharmaceutical verification information, the system comprising:
   a network;
   a server database;
   a server connected to the network and the server database, the server storing at least one known spectral signature of a known pharmaceutical and a corresponding known pharmaceutical name and dosage strength of the known pharmaceutical in the server database;
   a client database; and
   a pharmaceutical identification and verification system connected to the network and the client database, the pharmaceutical identification and verification system comprising a static multimode multiplex spectrometer and being capable of receiving the at least one known spectral signature and the corresponding known pharmaceutical name and dosage strength from the server, storing the at least one known spectral signature and the corresponding known pharmaceutical name and dosage strength in the client database, reading a pharmaceutical name and dosage strength from a container enclosing a pharmaceutical, obtaining a detected spectral signature for the pharmaceutical by performing an analysis of the pharmaceutical through the container, and comparing the detected spectral signature to the at least one known spectral signature.

2. The system of claim 1, wherein if the detected spectral signature matches the at least one known spectral signature, the pharmaceutical identification and verification system compares the pharmaceutical name and dosage strength to the known pharmaceutical name and dosage strength to verify the pharmaceutical.

3. The system of claim 2, wherein the pharmaceutical identification and verification system sends a signal to the server each time it obtains a spectral signature that is not verified.

4. The system of claim 1, wherein the container comprises one of a prescription vial, a manufacturer's bottle, and a wholesaler's bottle.

5. The system of claim 1, wherein if the detected spectral signature does not correspond to any spectral signatures in the client database, the pharmaceutical identification and verification system sends the detected spectral signature to the server.

6. The system of claim 5, wherein if the detected spectral signature does not correspond to any spectral signatures in the client database, the pharmaceutical identification and verification system sends a pharmaceutical name and dosage strength read from the container to the server.

7. The system of claim 1, wherein the pharmaceutical identification and verification system sends a transaction record to the server each time it obtains a spectral signature for a pharmaceutical.

8. The system of claim 1, wherein the server sends an update of the at least one known spectral signature to the pharmaceutical identification and verification system.

9. The system of claim 1, wherein the at least one known spectral signature comprises a spectral signature of a known container and the detected spectral signature comprises a spectral signature of the container.

10. The system of claim 1, wherein the detected spectral signature is produced by the static multimode multiplex spectrometer and the at least one known spectral signature is produced by a second static multimode multiplex spectrometer.

11. A method for communicating pharmaceutical verification information between a server and a pharmaceutical identification and verification system, the method comprising:
   the server storing at least one known spectral signature of a known pharmaceutical and a corresponding known pharmaceutical name and dosage strength of the known pharmaceutical in a server database connected to the server, the server being connected to a network;
   the pharmaceutical identification and verification system receiving the at least one known spectral signature and the corresponding known pharmaceutical name and dosage strength from the sewer, the pharmaceutical identification and verification system being connected to the network and a client database and comprising a static multimode multiplex spectrometer;
   the pharmaceutical identification and verification system storing the at least one known spectral signature and the corresponding known pharmaceutical name and dosage strength in the client database;
   the pharmaceutical identification and verification system reading a pharmaceutical name and dosage strength from a container enclosing a pharmaceutical;
   the pharmaceutical identification and verification system obtaining a detected spectral signature for the pharmaceutical by performing an analysis of the pharmaceutical through the container; and
   the pharmaceutical identification and verification system comparing the detected spectral signature to the at least one known spectral signature.

12. The method of claim 11, wherein the at least one known spectral signature comprises a spectral signature of a known container and the detected spectral signature comprises a spectral signature of the container.

13. The method of claim 11, wherein the detected spectral signature is produced by the static multimode multiplex spectrometer and the at least one known spectral signature is produced by a second static multimode multiplex spectrometer.

14. A system for communicating pharmaceutical verification information, the system comprising:
   a network;
   a server database;
   a server connected to the network and the server database, the server storing at least one known spectral signature comprising a spectral signature of a known pharmaceutical and a spectral signature of a known container in the server database and storing a corresponding known pharmaceutical name and dosage strength of the known pharmaceutical in the sewer database;
   a client database; and
   a pharmaceutical identification and verification system connected to the network and the client database, the pharmaceutical identification and verification system being capable of receiving the at least one known spectral signature and the corresponding known pharmaceutical name and dosage strength from the server, storing the at least one known spectral signature and the corresponding known pharmaceutical name and dosage strength in the client database, reading a pharmaceutical name and dosage strength from a container enclosing a pharmaceutical, obtaining a detected spectral signature comprising a spectral signature of the pharmaceutical and a spectral signature of the container by performing an analysis of the pharmaceutical through the container, and comparing the detected spectral signature to the at least one known spectral signature.

15. A method for communicating pharmaceutical verification information between a server and a pharmaceutical identification and verification system, the method comprising:
   the server storing at least one known spectral signature comprising a spectral signature of a known pharmaceutical and a spectral signature of a known container and a corresponding known pharmaceutical name and dosage strength of the known pharmaceutical in a server database connected to the sewer, the server being connected to a network;
   the pharmaceutical identification and verification system receiving the at least one known spectral signature and the corresponding known pharmaceutical name and dosage strength from the sewer, the pharmaceutical identification and verification system being connected to the network and a client database;
   the pharmaceutical identification and verification system storing the at least one known spectral signature and the corresponding known pharmaceutical name and dosage strength in the client database;
   the pharmaceutical identification and verification system reading a pharmaceutical name and dosage strength from a container enclosing a pharmaceutical;
   the pharmaceutical identification and verification system obtaining a detected spectral signature comprising a spectral signature of the pharmaceutical and a spectral signature of the container by performing an analysis of the pharmaceutical through the container; and
   the pharmaceutical identification and verification system comparing the detected spectral signature to the at least one known spectral signature.

16. A system for communicating pharmaceutical verification information, the system comprising:
   a network;
   a pharmaceutical identification and verification system connected to the network, the pharmaceutical identification and verification system comprising a static multimode multiplex spectrometer and being capable of reading a pharmaceutical name and dosage strength from a container enclosing a pharmaceutical and obtaining a detected spectral signature for the pharmaceutical by performing an analysis of the pharmaceutical through the container;
   a server database; and
   a server connected to the network and the server database, the server being capable of receiving the pharmaceutical name and dosage strength and the detected spectral signature from the pharmaceutical identification and verification system, comparing the detected spectral signature to one or more known spectral signatures of known pharmaceuticals in the server database to determine an identity of the pharmaceutical, comparing a known pharmaceutical name and dosage strength corresponding to a known spectral signature of a known pharmaceutical that matches the detected spectral signature to the pharmaceutical name and dosage strength to verify the pharmaceutical, and sending a result of the verification to the pharmaceutical identification and verification system.

17. The system of claim 16, wherein the container comprises one of a prescription vial, a manufacturer's bottle, and a wholesaler's bottle.

18. The system of claim 16, wherein the known spectral signature comprises a spectral signature of a known container and the detected spectral signature comprises a spectral signature of the container.

19. The system of claim 16, wherein the server records each detected spectral signature that is not verified.

20. A method for communicating pharmaceutical verification information between a server and a pharmaceutical identification and verification system, the method comprising:
   the pharmaceutical identification and verification system reading a pharmaceutical name and dosage strength from a container enclosing a pharmaceutical, the pharmaceutical identification and verification system being connected to a network and comprising a static multimode multiplex spectrometer;
   the pharmaceutical identification and verification system obtaining a detected spectral signature for the pharmaceutical by performing an analysis of the pharmaceutical through the container;
   the server receiving the pharmaceutical name and dosage strength and the detected spectral signature from the pharmaceutical identification and verification system, the server being connected to the network and a server database;
   the server comparing the detected spectral signature to one or more known spectral signatures of known pharmaceuticals in the server database to determine an identity of the pharmaceutical;
   the server comparing a known pharmaceutical name and dosage strength corresponding to a known spectral signature of a known pharmaceutical that matches the detected spectral signature to the pharmaceutical name and dosage strength to verify the pharmaceutical; and
   the server sending a result of the verification to the pharmaceutical identification and verification system.

21. The method of claim 20, wherein the known spectral signature comprises a spectral signature of a known container and the detected spectral signature comprises a spectral signature of the container.

22. The method of claim 20, further comprising the server recording each detected spectral signature that is not verified.

23. A system for communicating pharmaceutical verification information, the system comprising:
a network;
a pharmaceutical identification and verification system connected to the network, the pharmaceutical identification and verification system being capable of reading a pharmaceutical name and dosage strength of a prescription from a container enclosing a pharmaceutical and obtaining a detected spectral signature by performing an analysis of the pharmaceutical through the container, the detected spectral signature comprising a spectral signature of the pharmaceutical and a spectral signature of the container;
a server database; and
a server connected to the network and the server database, the server being capable of receiving the pharmaceutical name and dosage strength and the detected spectral signature from the pharmaceutical identification and verification system, comparing the detected spectral signature to one or more known spectral signatures in the sewer database to determine an identity of the pharmaceutical, comparing a known pharmaceutical name and dosage strength corresponding to a known spectral signature that matches the detected spectral signature to the pharmaceutical name and dosage strength to verify the pharmaceutical, and sending a result of the verification to the pharmaceutical identification and verification system, each of the one or more known spectral signatures comprising a spectral signature of a known pharmaceutical and a spectral signature of a known container.

24. The system of claim 23, wherein the server records each detected spectral signature that is not verified in the server database.

25. A method for communicating pharmaceutical verification information between a server and a pharmaceutical identification and verification system, the method comprising:
the pharmaceutical identification and verification system reading a pharmaceutical name and dosage strength of a prescription from a container enclosing a pharmaceutical, the pharmaceutical identification and verification system being connected to a network;
the pharmaceutical identification and verification system obtaining a detected spectral signature by performing an analysis of the pharmaceutical through the container, the detected spectral signature comprising a spectral signature of the pharmaceutical and a spectral signature of the container;
the server receiving the pharmaceutical name and dosage strength and the detected spectral signature from the pharmaceutical identification and verification system, the server being connected to the network and a server database;
the server comparing the detected spectral signature to one or more known spectral signatures in the server database to determine an identity of the pharmaceutical, each of the one or more known spectral signatures comprising a spectral signature of a known pharmaceutical and a spectral signature of a known container;
the server comparing a known pharmaceutical name and dosage strength corresponding to a known spectral signature that matches the detected spectral signature to the pharmaceutical name and dosage strength to verify the pharmaceutical; and
the server sending a result of the verification to the pharmaceutical identification and verification system.

26. The system of claim 25, further comprising the sewer recording each detected spectral signature that is not verified in the server database.

27. A method for distributing pharmaceutical verification information from a central sewer of a data provider to a pharmaceutical identification and verification system at a customer's location, the method comprising:
downloading the pharmaceutical verification information from the central server to a portable media device;
sending the portable media device to the customer's location; and
uploading the pharmaceutical verification information from the portable media device to the pharmaceutical identification and verification system wherein the pharmaceutical verification information comprises at least one known spectral signature of a known pharmaceutical obtained by performing an analysis of the pharmaceutical through a container.

28. The method of claim 27, wherein the pharmaceutical verification information comprises a known pharmaceutical name and dosage strength of the known pharmaceutical.

29. The method of claim 28, wherein the at least one known spectral signature comprises a spectral signature of a known pharmaceutical container.

30. The method of claim 29, wherein the known pharmaceutical container comprises one of a prescription vial, a manufacturer's bottle, and a wholesaler's bottle.

31. The method of claim 28, wherein the at least one known spectral signal is produced by a static multimode multiplex spectrometer.

32. The method of claim 27, wherein the pharmaceutical identification and verification system comprises a static multimode multiplex spectrometer.

33. The method of claim 27, where the portable media device comprises one of a compact disc read-only memory, a floppy disk, a magnetic tape, a flash memory drive, a flash memory card, a firmware device, a thumb-drive, and a universal serial bus drive.

34. The method of claim 27, wherein sending the portable media device to the customer's location comprises mailing the portable media device to the customer's location.

* * * * *